United States Patent
Rocco et al.

(10) Patent No.: US 7,683,062 B2
(45) Date of Patent: Mar. 23, 2010

(54) CRYSTALLINE FORM

(75) Inventors: William Rocco, Reading, PA (US); John D. Higgins, Phoenixville, PA (US)

(73) Assignee: sanofi-aventis U.S. LLC, Bridgewater, NJ (US)

(*) Notice: Subject to any disclaimer, the term of this patent is extended or adjusted under 35 U.S.C. 154(b) by 12 days.

(21) Appl. No.: 12/031,243

(22) Filed: Feb. 14, 2008

(65) Prior Publication Data

US 2008/0139569 A1  Jun. 12, 2008

Related U.S. Application Data

(63) Continuation of application No. PCT/US2006/033254, filed on Aug. 24, 2006.

(60) Provisional application No. 60/712,153, filed on Aug. 29, 2005.

(51) Int. Cl.
*A61K 31/5025* (2006.01)
*C07D 237/26* (2006.01)
*A61P 11/06* (2006.01)
*A61P 35/04* (2006.01)
*A61P 25/02* (2006.01)
*A61P 25/28* (2006.01)

(52) U.S. Cl. ................... 514/248; 544/234
(58) Field of Classification Search ........... 514/248; 544/234
See application file for complete search history.

(56) References Cited

U.S. PATENT DOCUMENTS 6,262,045 B1 * 7/2001 Evanno et al. ......... 514/210.18
6,395,729 B1 * 5/2002 Ferzaz et al. .............. 514/220

FOREIGN PATENT DOCUMENTS

FR              2829939       3/2003
WO       WO 2005/034999     4/2005

OTHER PUBLICATIONS

Ferzaz, B., et. al., SSR180575 (7-Chloro-N,N,5-Trimethyl-4-Oxo-3-Phenyl-3,5-Dihydro-4H-Pyridazino[4,5-b]Indole-1-Acetamide), A Peripheral Benzodiazepine Receptor Ligand, Promotes Neuronal Survival and Repair, The Journal of Pharmacology and Experimental Therapeutics, (2002) vol. 301, No. 3, pp. 1067-1078.
Galiegue, S., et. al., The Peripheral Benzodiazepine Receptor: A Promising Therapeutic Drug Target, Current Medicinal Chemistry, vol. 10, No. 16, (2003)—pp. 1563-1572.

* cited by examiner

*Primary Examiner*—James O Wilson
*Assistant Examiner*—Cecilia M Jaisle
(74) *Attorney, Agent, or Firm*—Kelly L. Bender (57) ABSTRACT

Disclosed are a novel crystalline form of 7-chloro-N,N,5-trimethyl-4-oxo-3-phenyl-3,5-dihydro-4H-pyridazino[4,5-b]indole-1-acetamide, processes of preparing said crystalline form of 7-chloro-N,N,5-trimethyl-4-oxo-3-phenyl-3,5-dihydro-4H-pyridazino[4,5-b]indole-1-acetamide, compositions comprising said form in admixture with one or more pharmaceutically acceptable excipients, and uses for the same.

11 Claims, 9 Drawing Sheets

CRYSTALLINE FORM

CROSS REFERENCE TO RELATED APPLICATIONS

This application is a continuation of International application No. PCT/US2006/033,254, filed Aug. 24, 2006; which claims the benefit of priority of U.S. Provisional Application No. 60/712,153, filed Aug. 29, 2005, both of which are incorporated herein by reference in their entirety.

BACKGROUND OF THE INVENTION

1. Field of the Invention

The present invention relates to a novel crystalline form, hereinafter referred to as crystalline Form II, of 7-chloro-N,N,5-trimethyl-4-oxo-3-phenyl-3,5-dihydro-4H-pyridazino[4,5-b]indole-1-acetamide.

This invention also relates to processes for the preparation of such crystalline form, and to methods of use thereof for the prevention and treatment of diseases related to peripheral-type benzodiazepine receptors.

2. Description of the Art

7-Chloro-N,N,5-trimethyl-4-oxo-3-phenyl-3,5-dihydro-4H-pyridazino[4,5-b]indole-1-acetamide, which has the structure of Formula (A):

(A)

possesses a high affinity for the peripheral-type benzodiazepine receptors. The preparation, physical properties and beneficial pharmacological properties of 7-chloro-N,N,5-trimethyl-4-oxo-3-phenyl-3,5-dihydro-4H-pyridazino[4,5-b]indole-1-acetamide are described in, for example, U.S. Pat. No. 6,262,045 and, in particular, U.S. Pat. No. 6,395,729, both of which are incorporated by reference in their entirety. The processes described in these patents result in the isolation of 7-chloro-N,N,5-trimethyl-4-oxo-3-phenyl-3,5-dihydro-4H-pyridazino[4,5-b]indole-1-acetamide in one defined crystalline form, herein designated as Form I.

The limited solubility of crystalline Form I of 7-chloro-N,N,5-trimethyl-4-oxo-3-phenyl-3,5-dihydro-4H-pyridazino[4,5-b]indole-1-acetamide in both aqueous solutions (generally less than 0.01 mg/ml) and non-aqueous formulation solvents (generally less than 3 mg/ml) presents difficulties in the administration and storage of formulations containing this compound. Preliminary studies carried out with standard formulations have led to limited absorption of the drug. Therefore, there is a need for new solid forms of 7-chloro-N,N,5-trimethyl-4-oxo-3-phenyl-3,5-dihydro-4H-pyridazino[4,5-b]indole-1-acetamide and new methods of their preparation.

SUMMARY OF THE INVENTION

We have discovered that the compound of Formula (A) can exist in the form of two crystalline polymorphs each having distinctly different physical properties. The two crystalline polymorphic forms described in this specification are hereinafter referred to as Form I and Form II.

Accordingly, the present invention relates to a crystalline polymorph Form II of 7-chloro-N,N,5-trimethyl-4-oxo-3-phenyl-3,5-dihydro-4H-pyridazino[4,5-b]indole-1-acetamide, represented by Formula (A) and to compositions comprising crystalline Form II. This invention also relates to processes for preparing crystalline Form II and to methods of use thereof.

DETAILED DESCRIPTION OF THE INVENTION

Definitions and Abbreviations

As used above, and throughout the description of the invention, the following abbreviations, unless otherwise indicated, shall be understood to have the following meanings:

Å Angstrom
HPLC high performance liquid chromatography
NMP N-methyl-2-pyrrolidinone
RPM revolutions per minute As used above, and throughout the description of the invention, the following terms, unless otherwise indicated shall be understood to have the following meanings.

Figure 2:
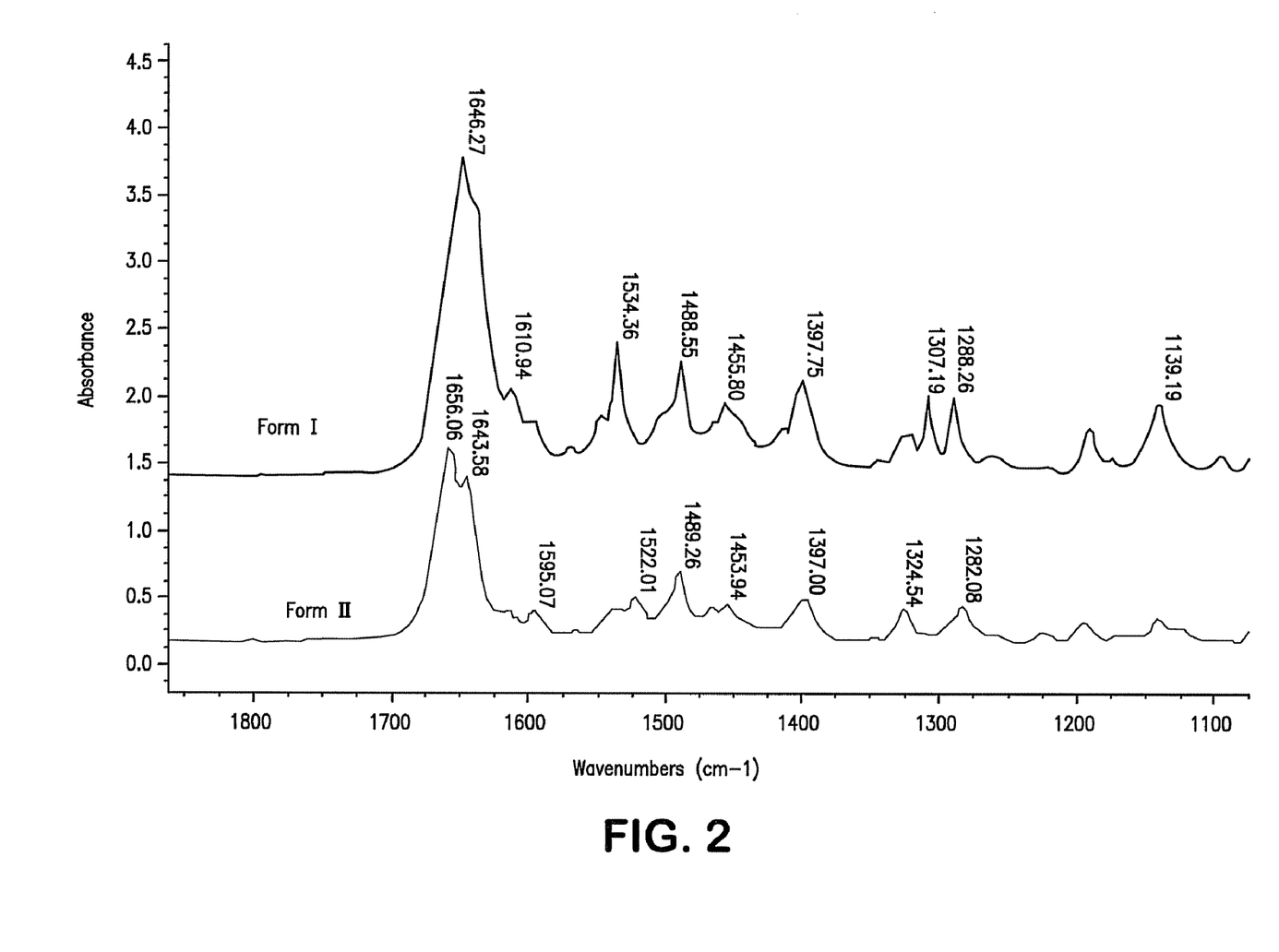
FIG. 2 is a Fourier Transform Infrared (FTIR) spectrum comparing crystalline Form I and crystalline Form II of 7-chloro-N,N,5-trimethyl-4-oxo-3-phenyl-3,5-dihydro-4H-pyridazino[4,5-b]indole-1-acetamide.
Figure 3:
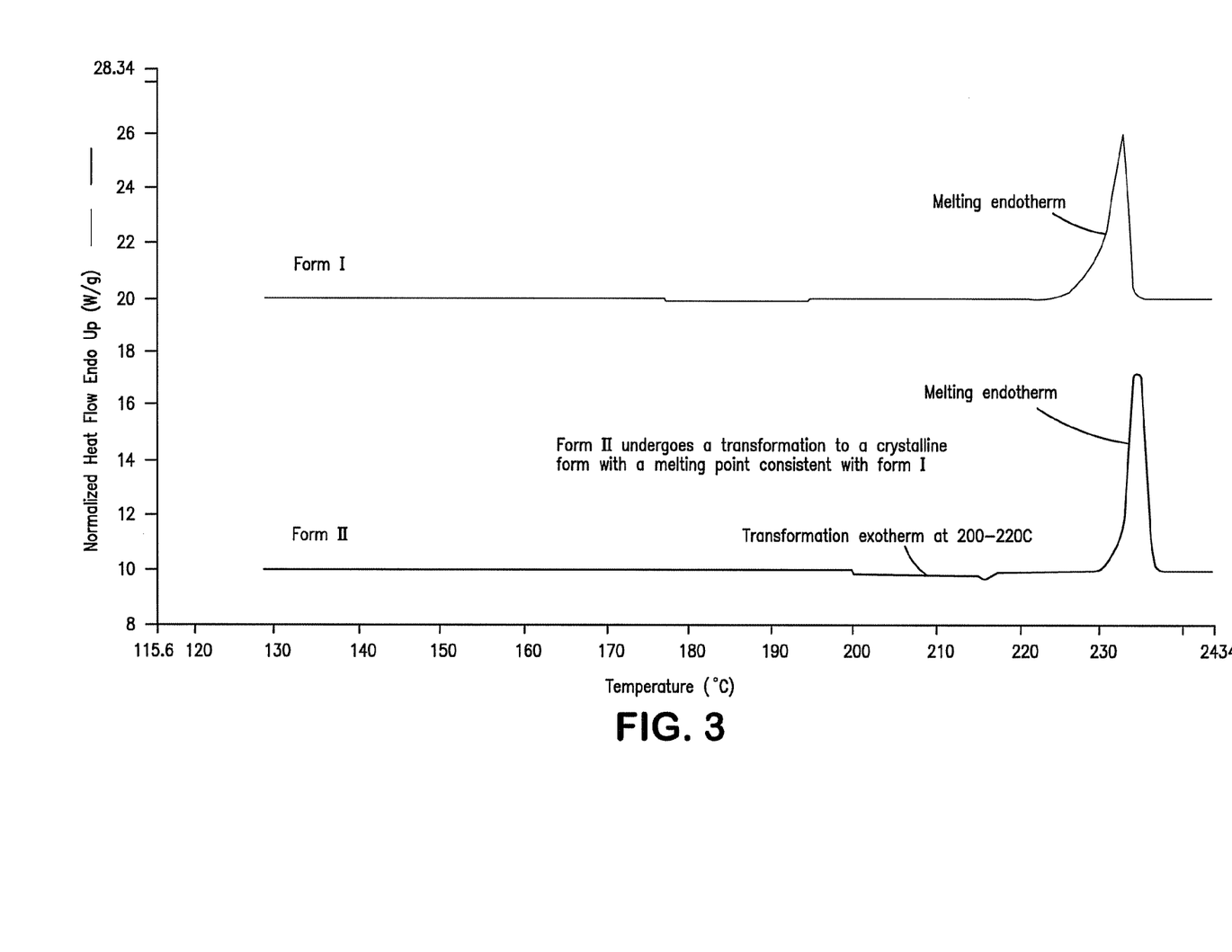
FIG. 3 is an overlay of Differential Scanning Calorimetry thermograms of crystalline Form I and crystalline Form II of 7-chloro-N,N,5-trimethyl-4-oxo-3-phenyl-3,5-dihydro-4H-pyridazino[4,5-b]indole-1-acetamide of this invention.
Figure 6:
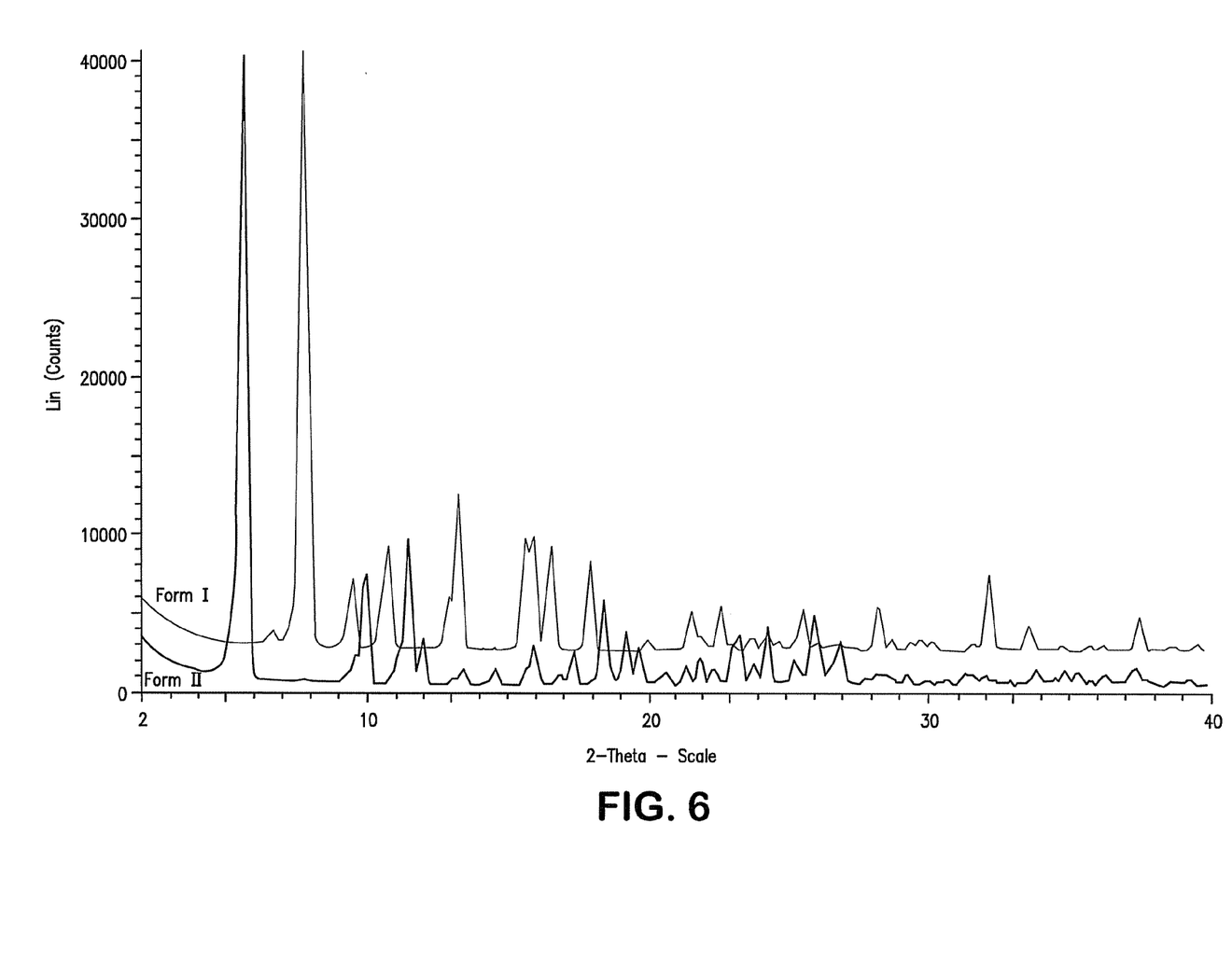
FIG. 6 is an overlay of X-ray powder diffractograms of crystalline Form I and crystalline Form II of 7-chloro-N,N,5-trimethyl-4-oxo-3-phenyl-3,5-dihydro-4H-pyridazino[4,5-b]indole-1-acetamide of the present invention.

"Form I," as used herein, is meant to describe a crystalline form of 7-chloro-N,N,5-trimethyl-4-oxo-3-phenyl-3,5-dihydro-4H-pyridazino[4,5-b]indole-1-acetamide that may be characterized using distinguishing data as described herein. Exemplary data is found in FIGS. 2, 3, and/or 6.

"Form II," as used herein, is meant to describe a crystalline form of 7-chloro-N,N,5-trimethyl-4-oxo-3-phenyl-3,5-dihydro-4H-pyridazino[4,5-b]indole-1-acetamide that may be characterized using distinguishing data as described herein. Exemplary data is found in FIGS. 1, 2, 3, 4, 5 and/or 6.

The ability of a substance to exist in more than one crystal form is defined as polymorphism; the different crystal forms of a particular substance are referred to as "polymorphs." In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance may possess different energies of the crystal lattice and, thus, in solid state they may show different physical properties such as form, density, melting point, color, stability, solubility, dissolution rate, et cetera which may, in turn, affect the stability, dissolution rate and/or bioavailability of a given polymorph and its suitability for use as a pharmaceutical and in pharmaceutical compositions.

Crystalline Form II of 7-chloro-N,N,5-trimethyl-4-oxo-3-phenyl-3,5-dihydro-4H-pyridazino[4,5-b]indole-1-acetamide has advantages over Form I. For example, Form II has greater solubility and higher dissolution rates than those of crystalline Form I. It is generally known that polymorphic forms having greater solubility and dissolution rates are usually less physically stable than those having lesser solubility and dissolution rates. However, crystalline Form II has surprising physical stability. For example, Form II does not convert into any other form under normal storage conditions (room temperature) or under the following stress conditions: 75% relative humidity at 50° C. for two months in an open vial. The stability of Form II under these conditions was confirmed by Fourier Transform IR spectroscopy data.

Thus, the present invention provides a novel crystalline form of 7-chloro-N,N,5-trimethyl-4-oxo-3-phenyl-3,5-dihydro-4H-pyridazino[4,5-b]indole-1-acetamide, which provides greater solubility than previously known crystalline Form I.

In a preferred aspect, the invention provides crystalline Form II of 7-chloro-N,N,5-trimethyl-4-oxo-3-phenyl-3,5-dihydro-4H-pyridazino[4,5-b]in dole-1-acetamide as herein defined substantially free of any other polymorph.

In a further preferred aspect, the crystalline Form II of 7-chloro-N,N,5-trimethyl-4-oxo-3-phenyl-3,5-dihydro-4H-pyridazino[4,5-b]indole-1-acetamide as herein defined is substantially free of impurities.

By "substantially free," it is meant that the crystalline Form II contains less than 10%, preferably less than 5%, and more preferably less than 2%, of any other polymorph or impurity or impurities.

Processes for the preparation of crystalline Form II are a further object of the present invention.

Crystalline Form II may be prepared by crystallization of 7-chloro-N,N,5-trimethyl-4-oxo-3-phenyl-3,5-dihydro-4H-pyridazino[4,5-b]indole-1-acetamide under suitable conditions.

Crystalline Form II may be prepared substantially free from crystalline Form I by controlling crystallization conditions.

In general, crystalline Form II may be obtained by heating 7-chloro-N,N,5-trimethyl-4-oxo-3-phenyl-3,5-dihydro-4H-pyridazino[4,5-b]indole-1-acetamide in a lower alcohol, for example methanol or ethanol, at a concentration of about 1 mg/ml to about 4 mg/ml and at a temperature sufficient to effect dissolution, for example about 45° C. to about 60° C., filtering any insolubles, cooling the filtrate, then evaporating the solvent with a stream of inert gas, such as nitrogen, to form a solid.

Alternatively, crystalline Form II is obtained via crystallization of 7-chloro-N,N,5-trimethyl-4-oxo-3-phenyl-3,5-dihydro-4H-pyridazino[4,5-b]indole-1-acetamide by dissolving the compound in dichloromethane at a concentration of about 30 mg/ml to about 50 mg/ml, adding the solution to ethanol, and concentrating the solution, reducing the volume by about 10% to about 40% with a stream of an inert gas, such as nitrogen gas, to cause precipitation of a solid.

In addition, crystalline Form II is obtained by dissolving 7-chloro-N,N,5-trimethyl-4-oxo-3-phenyl-3,5-dihydro-4H-pyridazino[4,5-b]indole-1-acetamide in dichloromethane at a concentration of about 20 mg/ml to about 50 mg/ml, adding the solution to hexanes to cause a precipitation of a solid, and isolating the solid such as by filtration.

Crystalline Form II may also be obtained utilizing other conventional techniques known to those skilled in the art for the preparation of crystalline forms, such as crystallization from a supercritical fluid, for example supercritical carbon dioxide.

The present invention is also directed to a pharmaceutical composition comprising crystalline Form II of 7-chloro-N,N,5-trimethyl-4-oxo-3-phenyl-3,5-dihydro-4H-pyridazino[4,5-b]indole-1-acetamide in combination with one or more pharmaceutically acceptable excipients. Preferred pharmaceutical compositions of the invention comprise crystalline Form II of 7-chloro-N,N,5-trimethyl-4-oxo-3-phenyl-3,5-dihydro-4H-pyridazino[4,5-b]indole-1-acetamide substantially free of crystalline Form I in combination with one or more pharmaceutically acceptable excipients.

In another embodiment, the present invention relates to dosage forms comprising the pharmaceutical compositions described herein. Dosage forms include, but are not limited to, those selected from the group consisting of pills, capsules, caplets, tablets, granules, suspensions, ointments, lotions, suppositories, and pastes. Each dosage should contain the quantity of drug substance calculated to produce the desired therapeutic effect. Typically, the pharmaceutical compositions will be administered in dosage units containing from about 2 mg to about 2000 mg of the drug substance by weight of the composition, with a range of about 10 mg to about 1000 mg being preferred.

The pharmaceutical compositions of the present invention preferably contain a therapeutically effective amount of the crystalline drug substance. The term "therapeutically effective amount," as used herein, refers to an amount of the drug substance present in the composition being administered that is sufficient to prevent development of, or alleviate to some extent, one or more of the symptoms of the disease being treated. Likewise, a therapeutically effective amount of a pharmaceutical composition refers to an amount of such composition that is sufficient to prevent development of or alleviate to some extent one or more of the symptoms of the disease being treated. In determining the effective amount or dose, a number of factors are considered by the attending diagnostician, including, but not limited to: the species of mammal; its size, age, and general health; the specific disease involved; the degree of involvement or the severity of the disease; the response of the individual patient; the mode of administration; the bioavailability characteristics of the preparation administered; the dose regimen selected; the use of concomitant medication; and other relevant circumstances.

The pharmaceutical compositions according to the present invention contain one or more pharmaceutically acceptable excipients generally used in the art. Such excipients may include one or more fillers; diluents, for example microcrystalline cellulose, lactose, mannitol, pregelatinized starch and the like; disintegrants, for example, sodium starch gylcolate, crospovidone, croscarmellose sodium and the like; lubricants, for example, magnesium stearate, sodium stearyl fumarate and the like; sweeteners, for example, sucrose, saccharin and the like; flavoring agents, for example, peppermint, methyl salicylate, orange flavoring and the like; colorants; preservatives; buffers; and other excipients depending on the route of administration and the dosage form used.

It will also be apparent to those skilled in the art that the pharmaceutical compositions of the present invention can be administered with other therapeutic and/or prophylactic agents and/or medicaments that are not medically incompatible therewith.

All components of the present compositions must be pharmaceutically acceptable. As used herein, a "pharmaceutically acceptable" component is one that is suitable for use with humans and/or other animals without undue adverse side effects (such as toxicity, irritation and allergic response) commensurate with a reasonable benefit/risk ratio.

The compositions of the present invention are generally administered to patients, which include, but are not limited to, mammals, for example, humans, by conventional routes known in the art. For example, the compositions can be administered to patients orally, in the form of, for example, a hard or soft gelatin capsule, a tablet, a caplet, or a suspension; rectally or vaginally, for example in the form of a tablet, suppository or pessary, paste, ointment, lotion, or suspension; or topically, for example in the form of a paste, ointment, lotion or suspension.

The present invention further relates to the use of the pharmaceutical compositions of the invention in medicine.

7-Chloro-N,N,5-trimethyl-4-oxo-3-phenyl-3,5-dihydro-4H-pyridazino[4,5-b]indole-1-acetamide possesses a high affinity for the peripheral-type benzodiazepine receptors and, as such, can be used for the prevention or treatment of peripheral neuropathies of different types, such as trauma-related or ischemic neuropathies, infectious, alcohol-related, drug-related or genetic neuropathies, as well as motoneuron conditions such as spinal amyotrophies and amyotrophic lateral sclerosis.

7-Chloro-N,N,5-trimethyl-4-oxo-3-phenyl-3,5-dihydro-4H-pyridazino[4,5-b]indole-1-acetamide may also be used for the prevention or treatment of neurodegenerative diseases of the central nervous system, either of the acute type such as cerebrovascular accidents and cranial and medullary traumas, or of the chronic type such as autoimmune diseases (multiple sclerosis), Alzheimer's disease, Parkinson's disease and any other disease in which the administration of neurotrophic factors is expected to have a therapeutic effect.

7-Chloro-N,N,5-trimethyl-4-oxo-3-phenyl-3,5-dihydro-4H-pyridazino[4,5-b]indole-1-acetamide may also be used for the prevention or treatment of acute or chronic renal insufficiency, glomerulonephritis, diabetic nephropathy, cardiac ischemia and insufficiency, myocardial infarction, ischemia of the lower limbs, coronary vasospasm, angina pectoris, pathological conditions associated with the cardiac valves, inflammatory cardiac diseases, side effects due to cardiotoxic medicaments or to the aftereffects of cardiac surgery, atherosclerosis and its thromboembolic complications, restenosis, graft rejections, conditions linked to incorrect proliferation or migration of the smooth muscle cells.

7-Chloro-N,N,5-trimethyl-4-oxo-3-phenyl-3,5-dihydro-4H-pyridazino[4,5-b]indole-1-acetamide has shown pharmacological activity in animal models of rheumatoid arthritis by modulating the immune response, and is therefore also useful for the prevention or treatment of rheumatoid arthritis.

Literature data indicates that the peripheral-type benzodiazepine receptor could play a fundamental role in regulating cell proliferation and cancerization processes. In general, and in comparison with normal tissues, an increased density of peripheral-type benzodiazepine receptors is observed in various types of tumors and cancer. Therefore, 7-chloro-N,N,5-trimethyl-4-oxo-3-phenyl-3,5-dihydro-4H-pyridazino[4,5-b]indole-1-acetamide may also be used for the prevention or treatment of tumors and cancers.

The peripheral-type benzodiazepine receptors are also present in the skin and, by virtue of these, 7-chloro-N,N,5-trimethyl-4-oxo-3-phenyl-3,5-dihydro-4H-pyridazino[4,5-b]indole-1-acetamide may be used for the prophylaxis or the treatment of cutaneous stresses. The expression cutaneous stress is understood to mean the various situations which could cause damage in particular in the epidermis, regardless of the agent causing this stress. This agent may be inside and/or outside the body, such as a chemical or free-radical agent, or else outside, such as ultraviolet radiation.

Therefore, the present invention relates to a method of treating and/or preventing diseases linked to the dysfunctioning of peripheral-type benzodiazepine receptors, which comprises administering to a patient in need of such treatment or prevention a therapeutically effective amount of crystalline Form II of the invention or a therapeutically effective amount of a pharmaceutical composition of the present invention.

In one embodiment, the present invention relates to a method of treating or preventing a neurodegenerative disease, which comprises administering to a patient in need of such treatment or prevention a therapeutically effective amount of crystalline Form II of the invention or a therapeutically effective amount of a pharmaceutical composition of the present invention.

Another embodiment of the present invention is a method of treating or preventing neuropathy, which comprises administering to a patient in need of such treatment or prevention a therapeutically effective amount of crystalline Form II of the invention or a therapeutically effective amount of a pharmaceutical composition of the present invention.

In another embodiment, the present invention relates to a method of treating or preventing cancer or tumors, which comprises administering to a patient in need of such treatment or prevention a therapeutically effective amount of crystalline Form II of the invention or a therapeutically effective amount of a pharmaceutical composition of the present invention.

Another embodiment of the invention is a method of treating or preventing cutaneous stresses, which comprises administering to a patient in need of such treatment or prevention a therapeutically effective amount of crystalline Form II of the invention or a therapeutically effective amount of a pharmaceutical composition of the present invention.

A preferred embodiment of the invention is a method of treating or preventing rheumatoid arthritis, which comprises administering to a patient in need of such treatment or prevention a therapeutically effective amount of crystalline Form II of the invention or a therapeutically effective amount of a pharmaceutical composition of the present invention.

Another preferred embodiment of the invention is a method for treating or preventing cardiac disease or a cardiac disorder, which comprises administering to a patient in need of such treatment or prevention a therapeutically effective amount of crystalline Form II of the invention or a therapeutically effective amount of a pharmaceutical composition of the present invention.

A subject of the present invention is the use of crystalline Form II of the invention in the manufacture of medicinal products for the treatment of diseases related to peripheral-type benzodiazepine receptors, such as neurodegenerative diseases, neuropathies, cancer or tumors, cutaneous stresses, rheumatoid arthritis or cardiac diseases or disorders.

The following examples will further illustrate the invention, without, however, limiting it thereto. Suitable 7-chloro-N,N,5-trimethyl-4-oxo-3-phenyl-3,5-dihydro-4H-pyridazino[4,5-b]indole-1-acetamide starting material for the herein described procedures includes, but is not limited to, 7-chloro-N,N,5-trimethyl-4-oxo-3-phenyl-3,5-dihydro-4H-pyridazino[4,5-b]indole-1-acetamide prepared by the procedures described in U.S. Pat. No. 6,395,729. Any form of 7-chloro-N,N,5-trimethyl-4-oxo-3-phenyl-3,5-dihydro-4H-pyridazino[4,5-b]indole-1-acetamide may be used as starting material for the preparation of Form II according to the procedures described herein. In some instances, such as for commercial scale synthesis, it may be advantageous to seed with Form II during the preparation.

EXAMPLE 1

Preparation of Crystalline Form I

7-Chloro-N,N,5-trimethyl-4-oxo-3-phenyl-3,5-dihydro-4H-pyridazino[4,5-b]indole-1-acetamide (230 g) was dissolved in N-methyl-2-pyrrolidinone (920 ml) at 110° C. Warm ethanol (2.5 L, 65° C.) was added to the solution, and a solid was isolated via filtration at 15° C. and washed with ethanol. The infrared spectra of crystalline Form I obtained substantially according to this procedure can be found in FIG. 2. The X-ray Powder Diffraction pattern can be found in FIG. 6.

EXAMPLE 2

Preparation of Crystalline Form II—Method A

Figure 1:
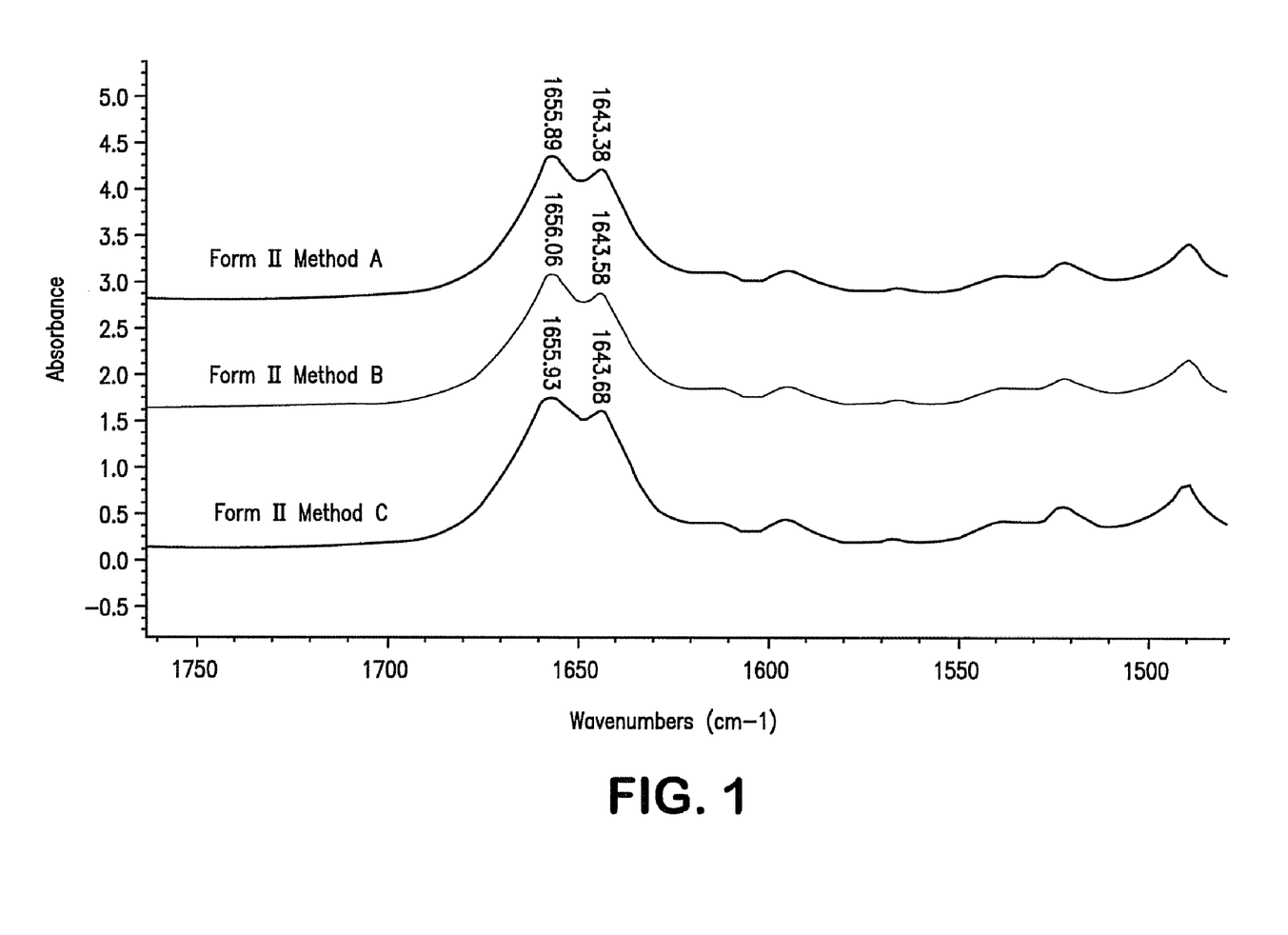
FIG. 1 is an overlay of three Fourier Transform Infrared (FTIR) spectra of crystalline Form II of 7-chloro-N,N,5-trimethyl-4-oxo-3-phenyl-3,5-dihydro-4H-pyridazino[4,5-b]indole-1-acetamide of the present invention.

7-Chloro-N,N,5-trimethyl-4-oxo-3-phenyl-3,5-dihydro-4H-pyridazino[4,5-b]indole-1-acetamide was dissolved in methanol at a concentration of 4 mg/ml at about 54° C. The solution was filtered hot, and the solvent was removed via evaporation using a stream of nitrogen, thus isolating a solid. Hot stage microscopy indicated a melting/transformation phenomenon at approximately 210° C. FIG. 1, Method A, is an IR spectrum of a sample substantially prepared according to this procedure.

EXAMPLE 3

Preparation of Crystalline Form II—Method B

Figure 4:
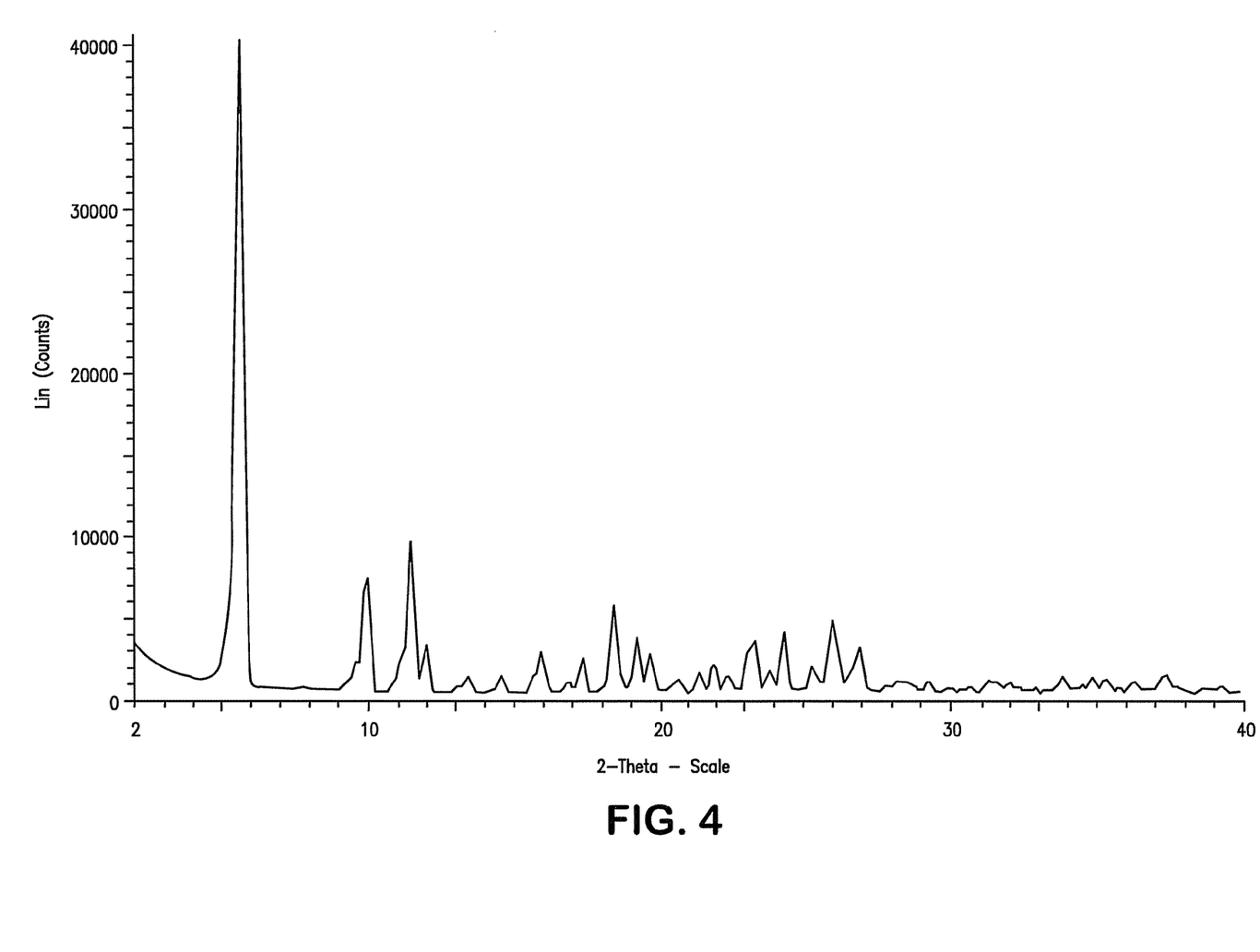
FIG. 4 is an X-ray powder diffractogram of crystalline Form II of 7-chloro-N,N,5-trimethyl-4-oxo-3-phenyl-3,5-dihydro-4H-pyridazino[4,5-b]indole-1-acetamide of the present invention.

7-Chloro-N,N,5-trimethyl-4-oxo-3-phenyl-3,5-dihydro-4H-pyridazino[4,5-b]indole-1-acetamide (1 g) was dissolved in 20 ml of dichloromethane (DCM) at room temperature. This solution was added to ethanol (70 ml) at room temperature. Nitrogen gas was used to concentrate the solution, reducing the volume by roughly 25%, to form a precipitate. The precipitate was isolated by filtration within approximately 15 to 30 minutes. FIG. 1, Method B, is an IR spectrum of a sample substantially prepared according to this procedure. FIG. 4 is an XRPD pattern of a sample substantially prepared according to this procedure.

EXAMPLE 4

Preparation of Crystalline Form II—Method C

Figure 5:
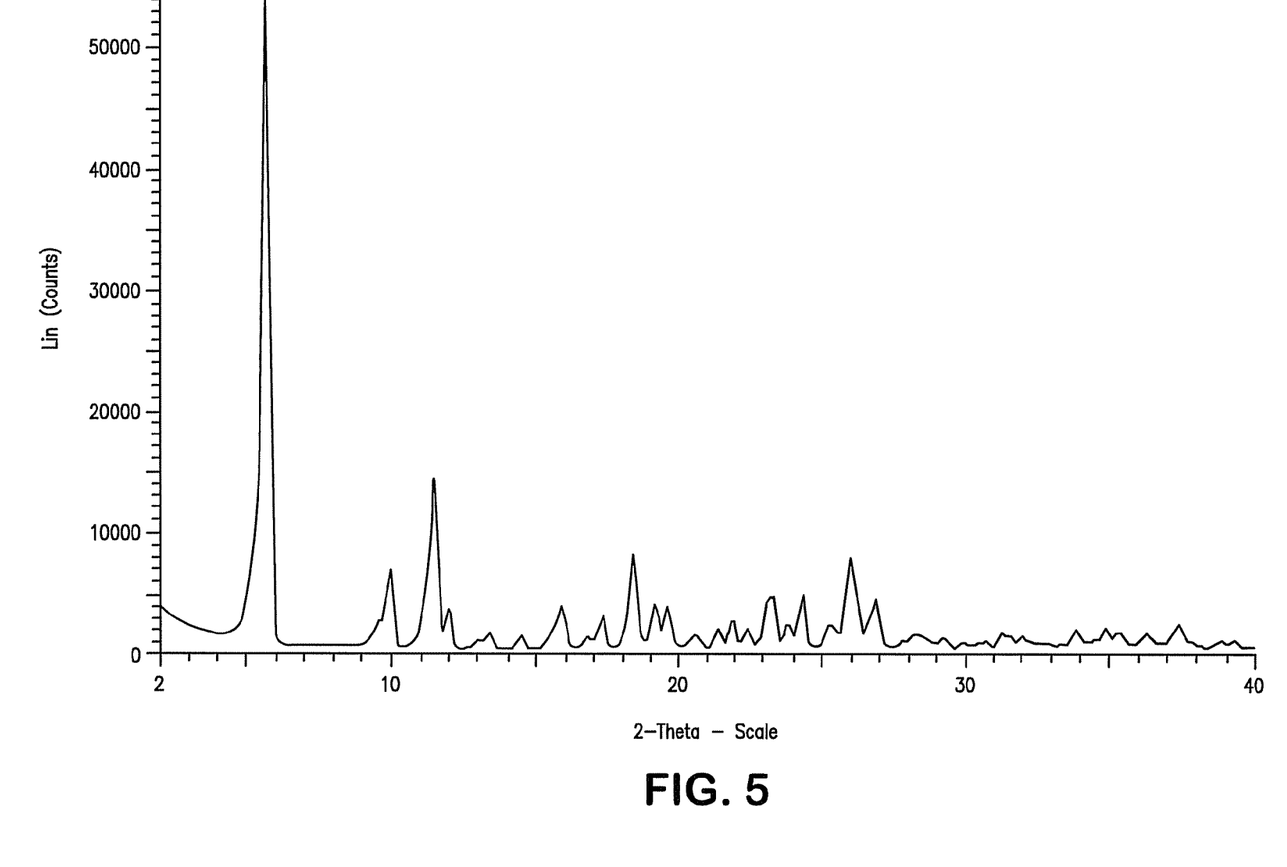
FIG. 5 is an X-ray powder diffractogram of crystalline Form II of 7-chloro-N,N,5-trimethyl-4-oxo-3-phenyl-3,5-dihydro-4H-pyridazino[4,5-b]indole-1-acetamide of the present invention.

7-Chloro-N,N,5-trimethyl-4-oxo-3-phenyl-3,5-dihydro-4H-pyridazino[4,5-b]indole-1-acetamide (2.4 g) was dissolved in dichloromethane (60 ml) at room temperature using a stirbar/plate. This solution was added slowly to hexanes (400 ml, HPLC grade) at room temperature with stirring. A precipitate formed immediately and was filtered after approximately 5 minutes. FIG. 1, Method C, is an IR spectrum of a sample substantially prepared according to this procedure. FIG. 5 is an XRPD pattern of a sample substantially prepared according to this procedure.

Portions of the IR spectra of the crystalline products prepared according to Examples 2 to 4 are overlaid in FIG. 1, indicating that these samples are of the same crystalline form.

The experiments below have been conducted on crystalline products prepared substantially according to the procedures described in Examples 1 to 4.

Experimentals

Fourier Transform Infrared Spectroscopy (FTIR)

Fourier Transform IR spectra were obtained with a Nicolet 750 Magna brand system. The drug substance was ground with dry potassium bromide (KBr) at a concentration of 1 mg drug substance/200 mg KBr and compressed into a disk (200 mg) at 10,000 lbs for analysis.

FTIR spectra (see FIG. 2) showed that Form II of 7-chloro-N,N,5-trimethyl-4-oxo-3-phenyl-3,5-dihydro-4H-pyridazino[4,5-b]indole-1-acetamide has peaks at approximately 1656, 1643 to 1644, 1595, 1522, 1489, 1454, 1397, 1325, and 1282 $cm^{-1}$. In particular, the peaks at 1656 and 1643 to 1644 $cm^{-1}$ are characteristic of Form II.

A comparison of the IR spectra (FIG. 2) of crystalline Form I and crystalline Form II shows two distinct patterns. Specifically, the amide region for Form II shows unique and characteristic peaks at approximately 1643 to 1644 $cm^{-1}$ and 1656 $cm^{-1}$, which are not present in the spectrum for Form I. In addition, the Form I band at approximately 1307 $cm^{-1}$ is not observed in any of the Form II samples described above.

Differential Scanning Calorimetry (DSC)

DSC scans were performed using a Perkin Elmer DSC-7 brand differential scanning calorimeter. The system was calibrated with indium and tin prior to use. The samples were encapsulated in aluminum pans (lids pierced). The DSC thermogram was acquired at a linear heating rate of 10° C. per minute.

The DSC scan for Form I (FIG. 3, upper curve) shows an endothermic peak at approximately 228° C. to 235° C., which corresponds to the melting point of Form I.

The DSC scan for Form II (FIG. 3, lower curve) shows conversion (transformation exotherm) to a higher melting crystalline form in the region of 200° C. to 220° C., followed by a melting endotherm that is consistent with the melting point of Form I. The shape of the DSC thermogram in the temperature region where conversion occurs is likely dependent upon heating rate, particle size and sample weight.

X-Ray Power Diffractometry (XRPD)

XRPD patterns were obtained with a Bruker D8® ADVANCE X-ray powder diffractometer using copper K-alpha radiation. The instrument was equipped with parallel beam optics, and the tube voltage and amperage were set to 40 kV and 40 mA, respectively. Samples were scanned at a rate of 1.0 degree/minute from 2 to 40 degrees in angle 2-theta.

Figure 7:
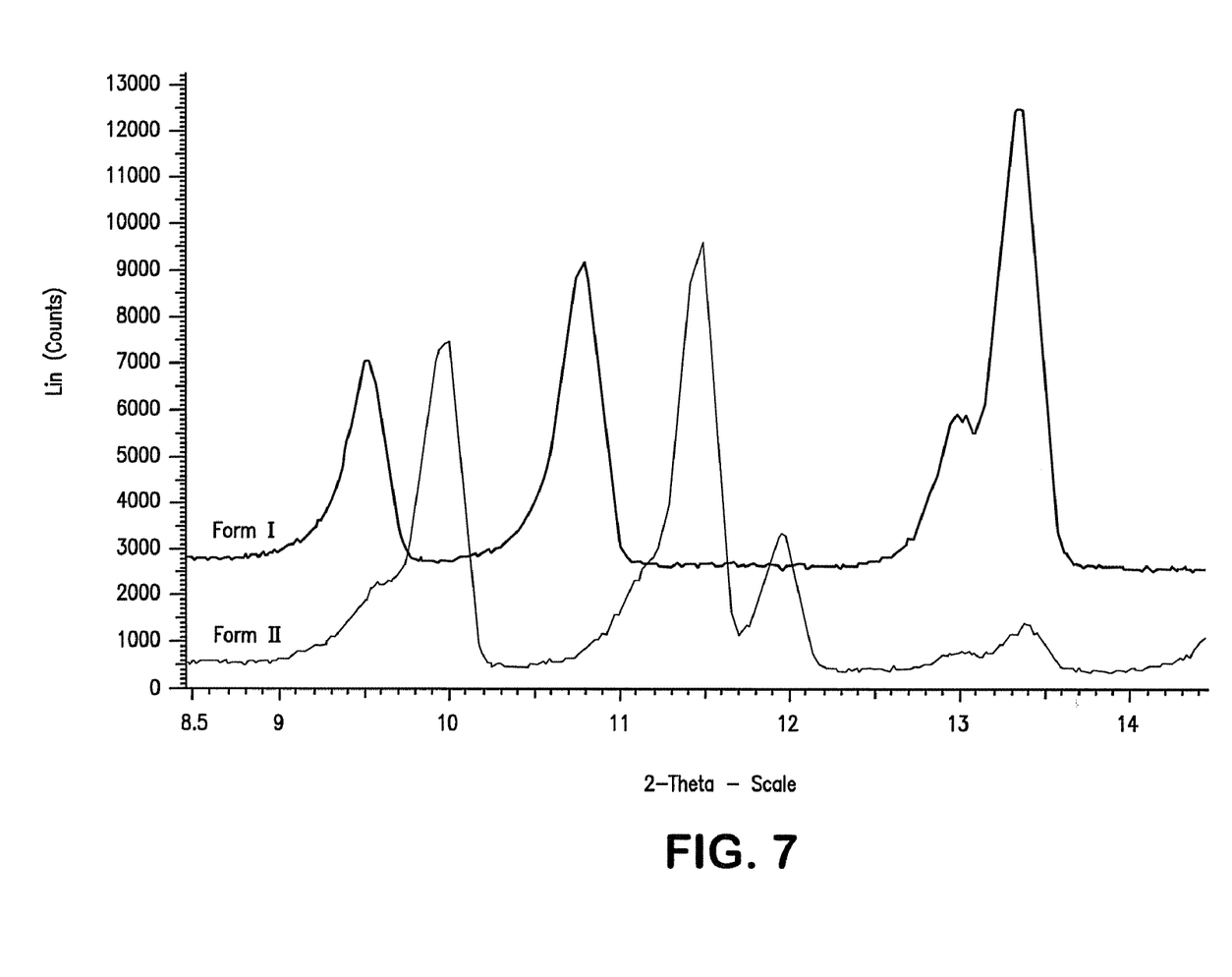
FIG. 7 is an overlay of X-ray powder diffractograms of crystalline Form I and crystalline Form II of 7-chloro-N,N,5-trimethyl-4-oxo-3-phenyl-3,5-dihydro-4H-pyridazino[4,5-b]indole-1-acetamide of the present invention.

FIG. 4 and FIG. 5 show identical XRPD patterns obtained for different samples of Form II, and FIG. 6 shows the XRPD pattern of Form II compared to the XRPD pattern of Form 1. The pattern for Form II shows a unique pattern relative to Form I. A characteristic peak at 5.71 degrees (2 theta) is observed in the pattern for Form II, but is not seen in the pattern for Form I. The absence of a peak at approximately 10.79 degrees (FIG. 7), a characteristic Form I peak, indicates that significant levels of Form I are not observed in the pattern for Form II.

A person skilled in the art will recognize that the peak locations could be slightly affected by differences in sample height. The peak locations described herein are thus subject to a variation of plus or minus (+/−) 0.15 degrees 2-theta. The relative intensities may change depending on the crystal size and morphology.

Table 1 sets forth the characteristic peak locations, d-spacings and relative intensities for the powder x-ray diffraction pattern for crystalline Form I.

TABLE 1

Characteristic XRPD Peak locations and Relative Intensities of Form II
Form II

| Angle<br>Degrees 2θ +/− 0.15°<br>2θ | Spacing<br>d value<br>(Angstroms) | Relative<br>Intensity<br>(%) |
|---|---|---|
| 19.21 | 4.6 | 9.3 |
| 18.43 | 4.8 | 14 |
| 15.95 | 5.6 | 7.3 |
| 11.97 | 7.4 | 8.2 |
| 11.47 | 7.7 | 23.8 |
| 9.97 | 8.9 | 18.2 |
| 5.71 | 15.5 | 100 |

In particular, the peaks (expressed in degrees 2-theta+/− 0.15 degrees 2-theta) at 11.47, 9.97, and 5.71 are characteristic of Form II.

Table II sets forth the characteristic peak locations, d-spacings and relative intensities for the powder x-ray diffraction pattern for crystalline Form I.

TABLE 2

XRPD Peak locations and Relative Intensities of Form I
Form I

| Angle<br>Degrees 2θ +/− 0.15°<br>2θ | Spacing<br>d value<br>(Angstroms) | Relative<br>Intensity<br>(%) |
|---|---|---|
| 18.05 | 4.9 | 23.1 |
| 16.67 | 5.3 | 24.8 |
| 16.00 | 5.5 | 25.8 |
| 15.79 | 5.6 | 25.3 |
| 13.36 | 6.6 | 31.1 |
| 10.79 | 8.2 | 24.8 |
| 7.85 | 11.2 | 100 |

Dissolution Testing

Dissolution tests of crystalline Form I and crystalline Form II were conducted with a paddle-type drug dissolution testing bath (available from Distek Inc.) at 75 RPM and a HP 8453 UV brand spectrophotometer at a wavelength of 320 nm. The following parameters were used: the drug substance concentration was 40 mg/L media, the dissolution media was 0.25% sodium lauryl sulfate/0.01M pH 7 phosphate buffer, the temperature was 37° C., and the sampling time was 10 minutes. Standards were prepared by diluting a stock solution in methanol (0.25 mg/ml) with dissolution media.

Figure 8:
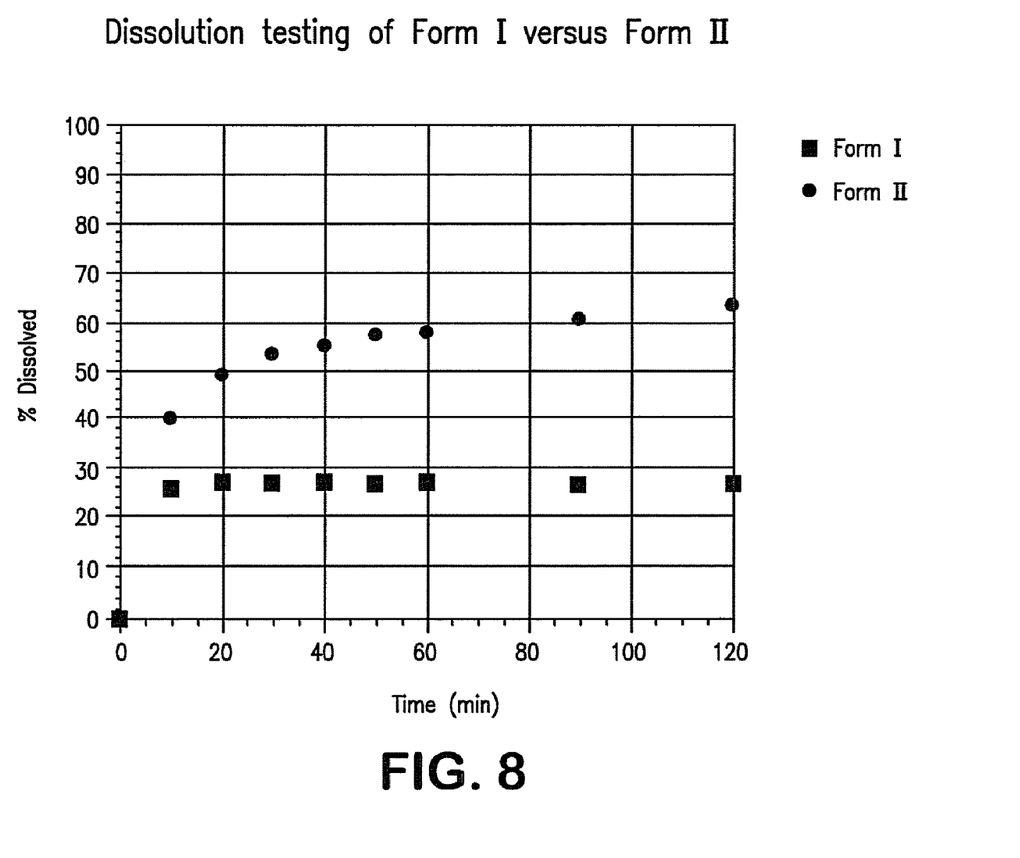
FIG. 8 shows dissolution testing results comparing the solubility/dissolution rates of crystalline Form I and crystalline Form II of 7-chloro-N,N,5-trimethyl-4-oxo-3-phenyl-3,5-dihydro-4H-pyridazino[4,5-b]indole-1-acetamide in aqueous 0.25% sodium lauryl sulfate/0.01 M pH 7 phosphate buffer.

The results of dissolution testing, which are shown in FIG. 8, indicate that crystalline Form II has greater solubility/dissolution in aqueous 0.25% sodium lauryl sulfate/phosphate buffer.

Stability Testing

Samples of Form II were stored at 50° C./75% relative humidity (open glass vials) to determine if polymorphic changes would be observed. Samples were analyzed at 2 months. The chamber humidity was controlled via a saturated sodium chloride aqueous solution.

Figure 9:
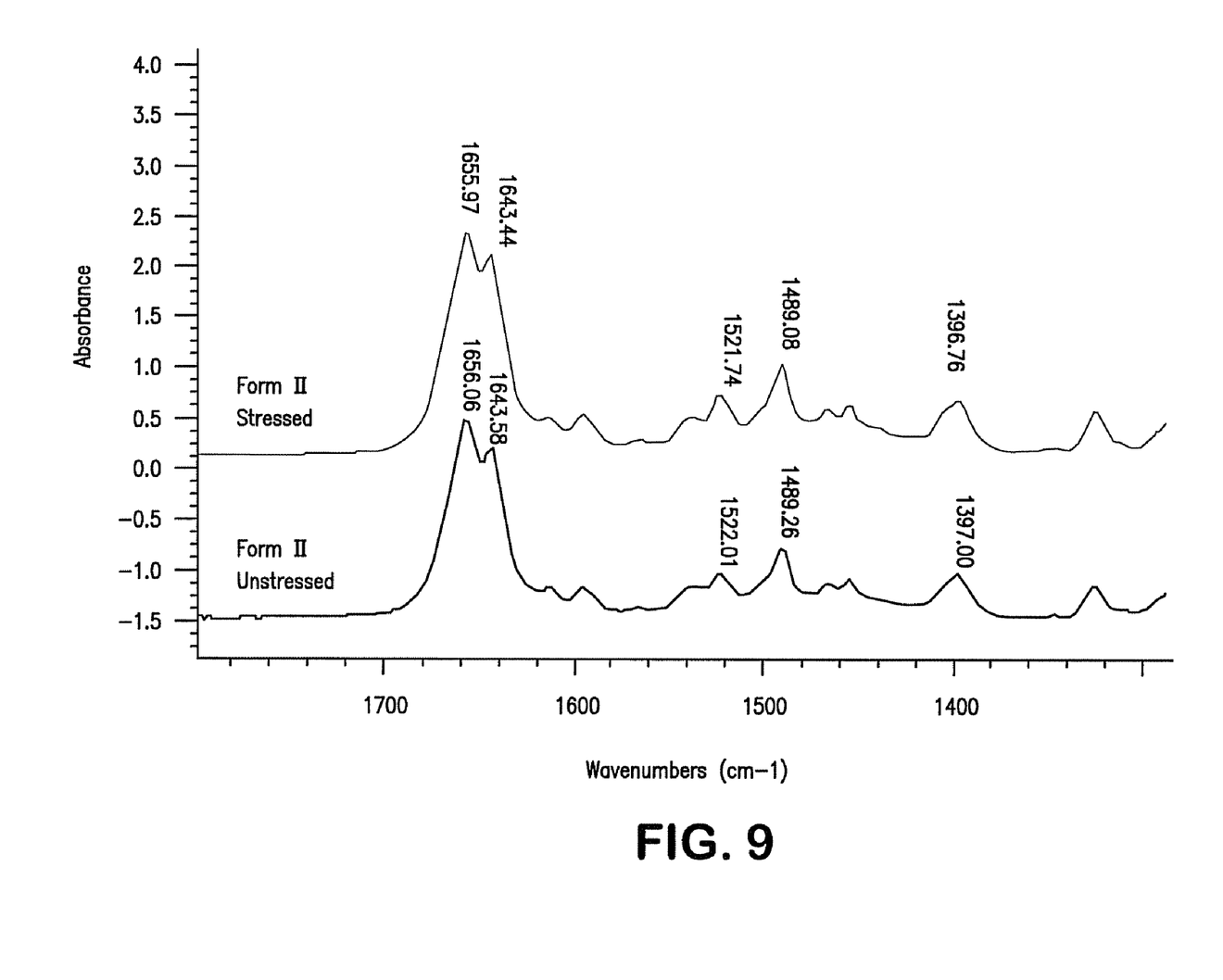
FIG. 9 is an overlay of Fourier Transform-Infrared (FT-IR) spectra of crystalline Form II of 7-chloro-N,N,5-trimethyl-4-oxo-3-phenyl-3,5-dihydro-4H-pyridazino[4,5-b]indole-1-acetamide of the present invention under unstressed and stressed conditions.

The FTIR spectra (FIG. 9) of the Form II sample after two months at 50° C./75% relative humidity (stressed) showed no changes indicative of conversion to Form I. The sample shows no evidence of conversion to Form I under extreme stressing; the characteristic Form I absorbance band at 1307 cm$^{-1}$ (shown in FIG. 2) remains absent.

These results indicate that no significant differences are present between the stressed and unstressed (initial) samples.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A crystalline form of a compound of Formula (A):

(A)

which is designated Form II.

2. The crystalline form of 7-chloro-N,N,5-trimethyl-4-oxo-3-phenyl-3,5-dihydro-4H-pyridazino[4,5-b]indole-1-acetamide according to claim 1 that exhibits an X-ray diffraction pattern comprising a peak at about 5.71 degrees 2-theta.

3. The crystalline form according to claim 2, wherein the X-ray diffraction pattern further comprises peaks at about: 11.47 and 9.97 degrees 2-theta.

4. The crystalline form according to claim 3, wherein the X-ray diffraction pattern further comprises peaks at about: 19.21, 18.43, 15.95, and 11.97 degrees 2-theta.

5. The crystalline form according to claim 1 substantially free of any other polymorph of a compound of Formula (A).

6. A pharmaceutical composition comprising the crystalline form according to claim 1 and one or more pharmaceutically acceptable excipients.

7. A pharmaceutical composition comprising the crystalline form according to claim 2 and one or more pharmaceutically acceptable excipients.

8. A pharmaceutical composition comprising the crystalline form according to claim 3 and one or more pharmaceutically acceptable excipients.

9. A process of preparing the crystalline form of claim 1, said process comprising the steps of:
 a) mixing 7-chloro-N,N,5-trimethyl-4-oxo-3-phenyl-3,5-dihydro-4H-pyridazino[4,5-b]indole-1-acetamide with a lower alcohol at a concentration of about 1 mg/ml to about 4 mg/ml to form a mixture,
 b) heating the mixture to a temperature between about 45° C. and about 60° C.;
 c) filtering the mixture, and
 d) evaporating the lower alcohol in the filtrate with a stream of inert gas to form a solid.

10. A process of preparing the crystalline form of claim 1, said process comprising the steps of:
 a) dissolving 7-chloro-N,N,5-trimethyl-4-oxo-3-phenyl-3,5-dihydro-4H-pyridazino[4,5-b]indole-1-acetamide in dichloromethane at a concentration of about 30 mg/ml to about 50 mg/ml to form a solution;
 b) adding the solution to ethanol at a ratio of about 1:3 to about 1:4 by volume relative to the amount of dichloromethane;
 c) concentrating the solution, reducing the volume by about 10% to about 40%, with a stream of inert gas until a solid crystallizes; and
 d) isolating the solid.

11. A process of preparing the crystalline form of claim 1, said process comprising the steps of:
 a) dissolving 7-chloro-N,N,5-trimethyl-4-oxo-3-phenyl-3,5-dihydro-4H-pyridazino[4,5-b]indole-1-acetamide in dichloromethane at a concentration of about 20 mg/ml to about 50 mg/ml to form a solution,
 b) adding the solution to hexanes to cause a precipitation of a solid, and isolating the solid.

* * * * *

UNITED STATES PATENT AND TRADEMARK OFFICE
CERTIFICATE OF CORRECTION

| | | |
|---|---|---|
| PATENT NO. | : 7,683,062 B2 | Page 1 of 1 |
| APPLICATION NO. | : 12/031243 | |
| DATED | : March 23, 2010 | |
| INVENTOR(S) | : William Rocco et al. | |

It is certified that error appears in the above-identified patent and that said Letters Patent is hereby corrected as shown below:

In column 9, line 45, delete "Form I." and insert -- Form II. --, therefor.

Signed and Sealed this

Eleventh Day of January, 2011

David J. Kappos
*Director of the United States Patent and Trademark Office*